United States Patent [19]
Spratt

[11] Patent Number: 5,838,592
[45] Date of Patent: Nov. 17, 1998

[54] METHOD AND APPARATUS FOR MEASURING FETUS HEAD AND ABDOMINAL CIRCUMFERENCE

[75] Inventor: Ray Steven Spratt, San Jose, Calif.

[73] Assignee: Diasonics Ultrasound Inc., Santa Clara, Calif.

[21] Appl. No.: 730,106

[22] Filed: Oct. 14, 1996

[51] Int. Cl.⁶ ........................................................ A61B 8/00
[52] U.S. Cl. .......................... 364/560; 600/407; 600/437; 600/443; 387/181
[58] Field of Search ........................ 364/560; 128/660.01, 128/660.06, 660.07, 662.02; 73/1.82, 703; 340/943; 382/181; 600/443, 407, 437

[56] References Cited

U.S. PATENT DOCUMENTS

5,588,435  12/1996  Weng et al. ........................ 128/660.07
5,605,155  2/1997  Chalana et al. .................... 128/660.07

*Primary Examiner*—James P. Trammell
*Assistant Examiner*—Patrick Assouad
*Attorney, Agent, or Firm*—Blakely Sokoloff Taylor & Zafman

[57]  ABSTRACT

A method and apparatus for automatically measuring the circumference of a first region enclosed in a second region internal to a living organism, wherein the first and second regions consist of different cellular matter. One embodiment of the present invention includes generating a point inside an interior of the first region. A set of radial vectors are then generated, which emanate from the point in the interior of the first region. A path is then selected which intersects the set of radial vectors. The path is selected by identifying a distinguishable ultrasonic measurement along the respective radial vectors. A length of the selected path is then measured to generate the circumference of the first region.

18 Claims, 8 Drawing Sheets

METHOD AND APPARATUS FOR MEASURING FETUS HEAD AND ABDOMINAL CIRCUMFERENCE

FIELD OF THE INVENTION

The present invention relates to ultrasonic measurement equipment, and more specifically, to a method and apparatus for measuring fetus head and abdominal circumference.

BACKGROUND

A number of measurements using ultrasound images can be taken during various stages of fetus development. Among the measurements are the head circumference, the abdominal circumference, and the bipolar diameters of these regions and other regions. These measurements can be used to estimate the gestational age of the fetus. Given the gestational age, this type of information can be checked against established growth curves to help diagnosis abnormalities and diseases of the fetus.

Generating these measurements, however, can be very time consuming for a machine operator. Moreover, the accuracy of the measurements are very dependent on the skill of the operator generating the measurements.

Consider an example of a conventional method for measuring the head circumference of a fetus. After the sonographer has generated the appropriate image, they typically locate a caliper at one end of an axis of the head's image and then align another caliper at a diametrically opposed location. An ellipse is then generated and adjusted it until it encloses the head of the fetus. Small iterative adjustments are made to the end points and width of the ellipse until it best approximates the shape of the head. When measuring the abdominal circumference of a fetus, many of the same steps are carried out in a similar manner.

Therefore, considering the length and the complexity typically involved in measuring the head and abdominal circumference of a fetus, it is desirable to have a method and apparatus for automatically determining these measurements to eliminate some of the dependency on the skills of an operator and to increase the speed of generating the measurements.

SUMMARY OF THE INVENTION

The present invention provides a method and apparatus for automatically measuring the circumference of a first region enclosed in a second region internal to a living organism, wherein the first and second regions consist of different cellular matter. One embodiment of the present invention includes generating a point inside an interior of the first region. A set of radial vectors are then generated, which emanate from the point in the interior of the first region. A path is then selected which intersects the set of radial vectors. The path is selected by identifying a distinguishable ultrasonic measurement along the respective radial vectors. A length of the selected path is then measured to generate the circumference of the first region.

BRIEF DESCRIPTION OF THE DRAWINGS

One embodiment of present invention is illustrated by way of example, and not by way of limitation, in the figures of the accompanying drawings and in which like reference numerals refer to similar elements and in which.

DETAILED DESCRIPTION

A method and apparatus is described for measuring the circumference of internal anatomical regions including the head and abdominal sections of a fetus. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

In one embodiment of the present invention, in an ultrasound image the circumference of a first region shown enclosed in a second region internal to a living organism is measured, wherein the first and second regions consist of different cellular matter. The circumference is measured by selecting a center point within the first region and generating a set of radial vectors emanating from the center point. A common path intersecting the radial vectors is then selected, which is assumed to represent the edge of the first region. The common path is selected by locating a distinguishable ultrasonic measurement along each radial vector. The accuracy of selecting the path which represents the edge of the first region in increased by selecting a path that consist of generally smooth curves. That is, in the selected path, in the vertical difference where the path intersects adjacent radial vectors is minimal.

The length of the selected path may then be used to determine the circumference of the first region. In alternative embodiments, the selected path can be fitted into an ellipse representing the edge of the first region, and a bipolar diameter (BPD) measurement of the ellipse can be generated using the short axis of the ellipse, with one end of the diameter measured from the inside of the ellipse.

Figure 1:
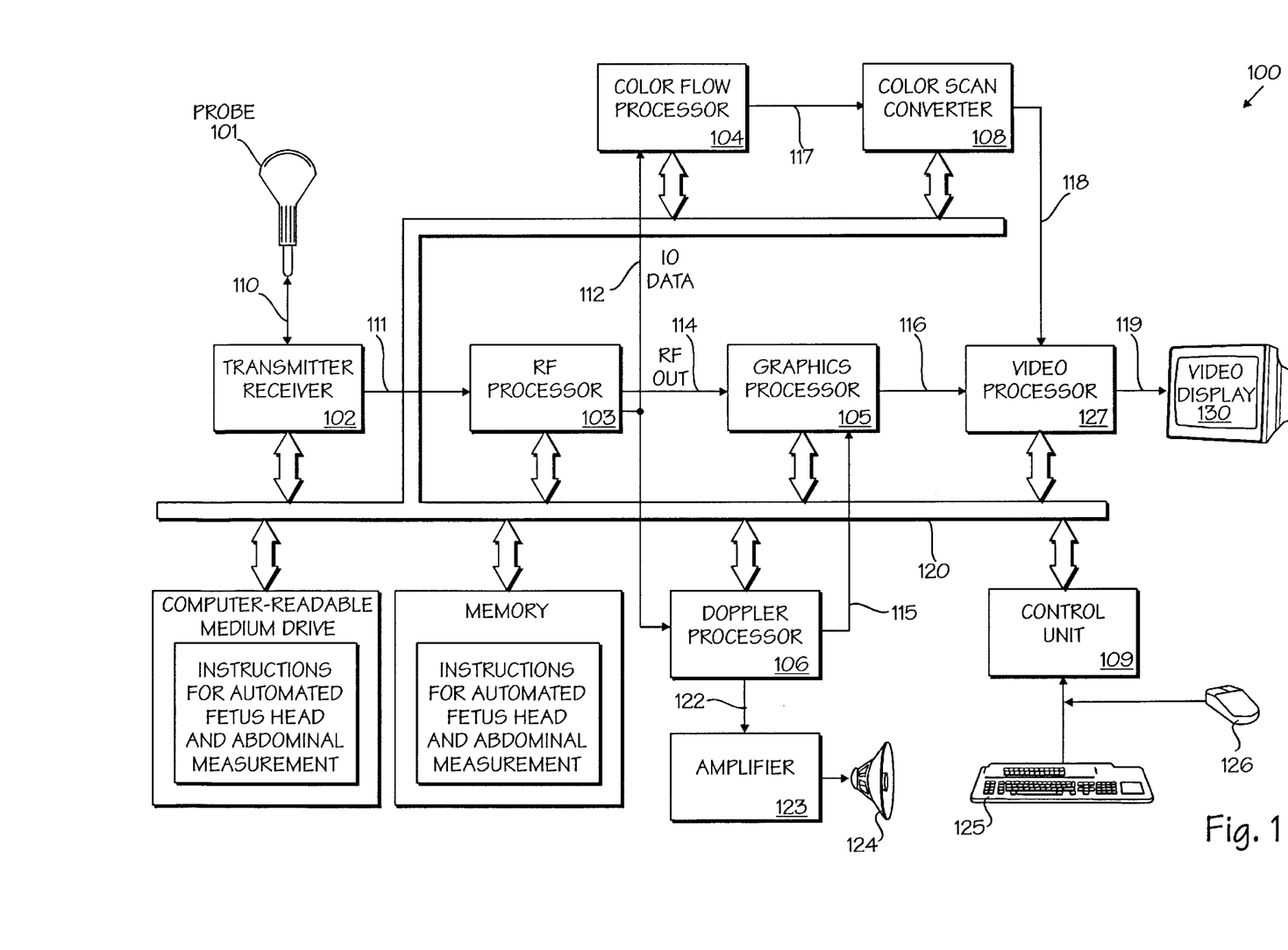
FIG. 1 is a block diagram of an ultrasonic system capable of implementing one embodiment of the present invention.

Referring to FIG. 1, an ultrasonic system capable of implementing one embodiment of the present invention is illustrated as ultrasonic system 100. Ultrasonic system 100 generally comprises a probe 101 which is coupled via line 110 to transmitter/receiver circuitry 102. Transmitter/receiver circuitry 102 is designed so that the elements of probe 101 will be fired at specified time intervals, with reflective pulses being detected using probe 101 at another given time interval. Transmitter/receiver circuitry 102 is coupled to control unit 109 via bus 120. Control unit (or host computer) 109 controls circuitry in the imaging system via bus 120. Control unit 109 is further coupled to a keyboard 125 and a mouse, trackball or other device cursor control 126 for movement and control information shown on video display 130 and for entering information and/or request to control unit 109.

Once a pulse is received by transmitter/receiver circuitry 102, such information is transmitted by line 111 to radio frequency (RF) processor 103 for further processing. The radio frequency information (in-phase (I) and quadrature (Q) signals) is further transmitted via line 114 to graphics processor 105 and to Doppler processor 106 via lines 114 and 112, respectively. Information generated by Doppler processor 106 is transmitted via line 115 to graphics processor 105. Graphics processor 105 transmits scan line information to video processor 127 via line 116 for generation of black and white ultrasound information on video display 130. Such information may be transmitted in National Television Standards Committee (NTSC) format and thus be stored on video tape for later clinical examination by attending medical personnel. In addition to information passed to graphics processor 105 and Doppler processor 106, RF processor 103 transmits I and Q signals via line 12 to color flow processor 104. Color flow processor 104 is also controlled by control unit 109 via bus 120. Color flow processor 104 detects Doppler shift and blood flow information in living tissue, and thus transmits this information via line 117 to color scan converter 108. Color scan converter 108 interpolates point scan line information obtained from color flow processor 104, and transmits that information on line 118 to video processor 127 for representation of blood flow in the human body, which can be used to distinguish between separate regions inside of a living organism, where the separate regions may consist of different cellular matter and have different echoginicity.

The methods of the present invention may be operative either within the graphics processor 105 or the color processor 104, processing image data.

Figure 2:
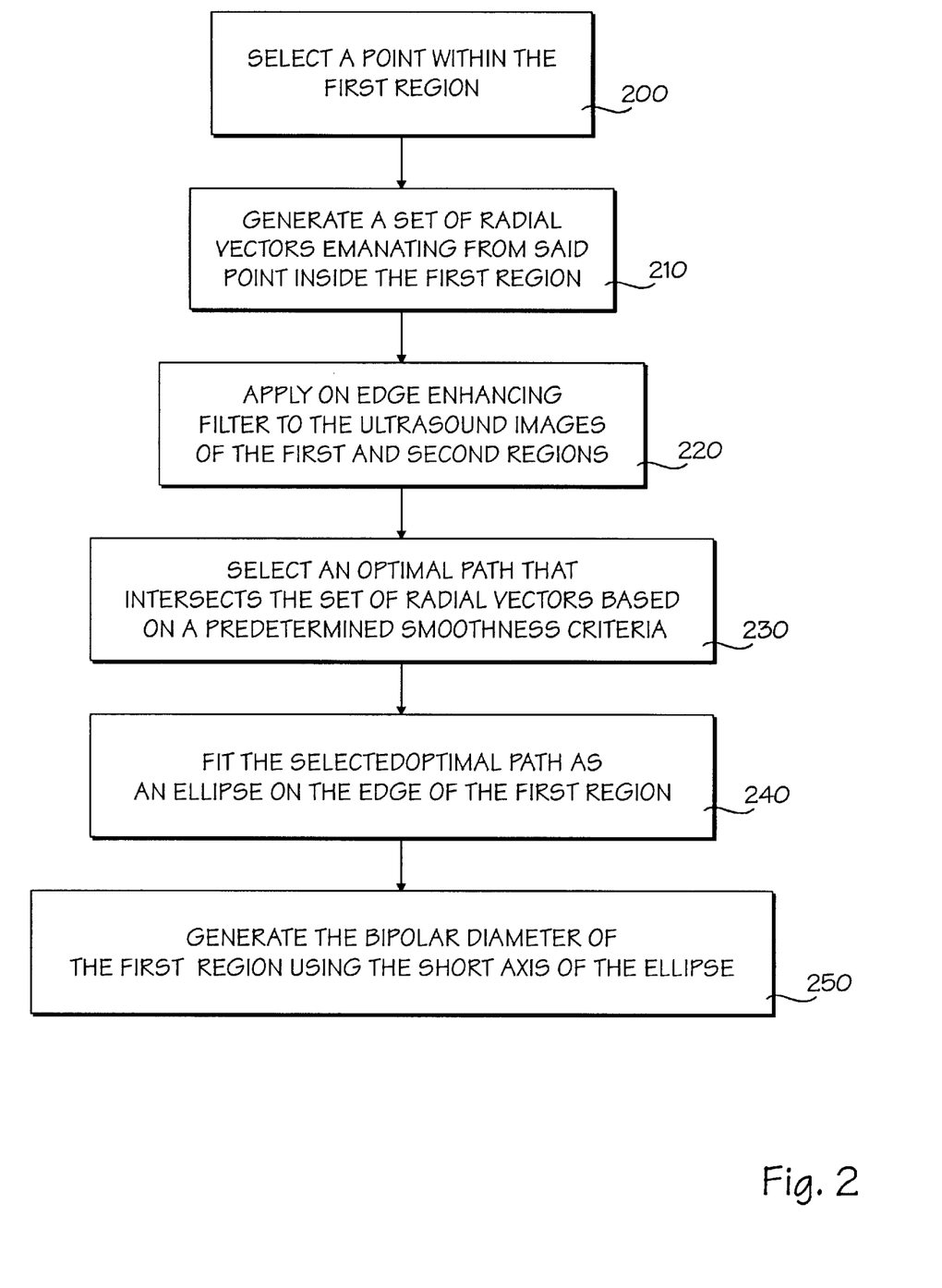
FIG. 2 is a flow diagram for one embodiment of the present invention.
Figure 3:
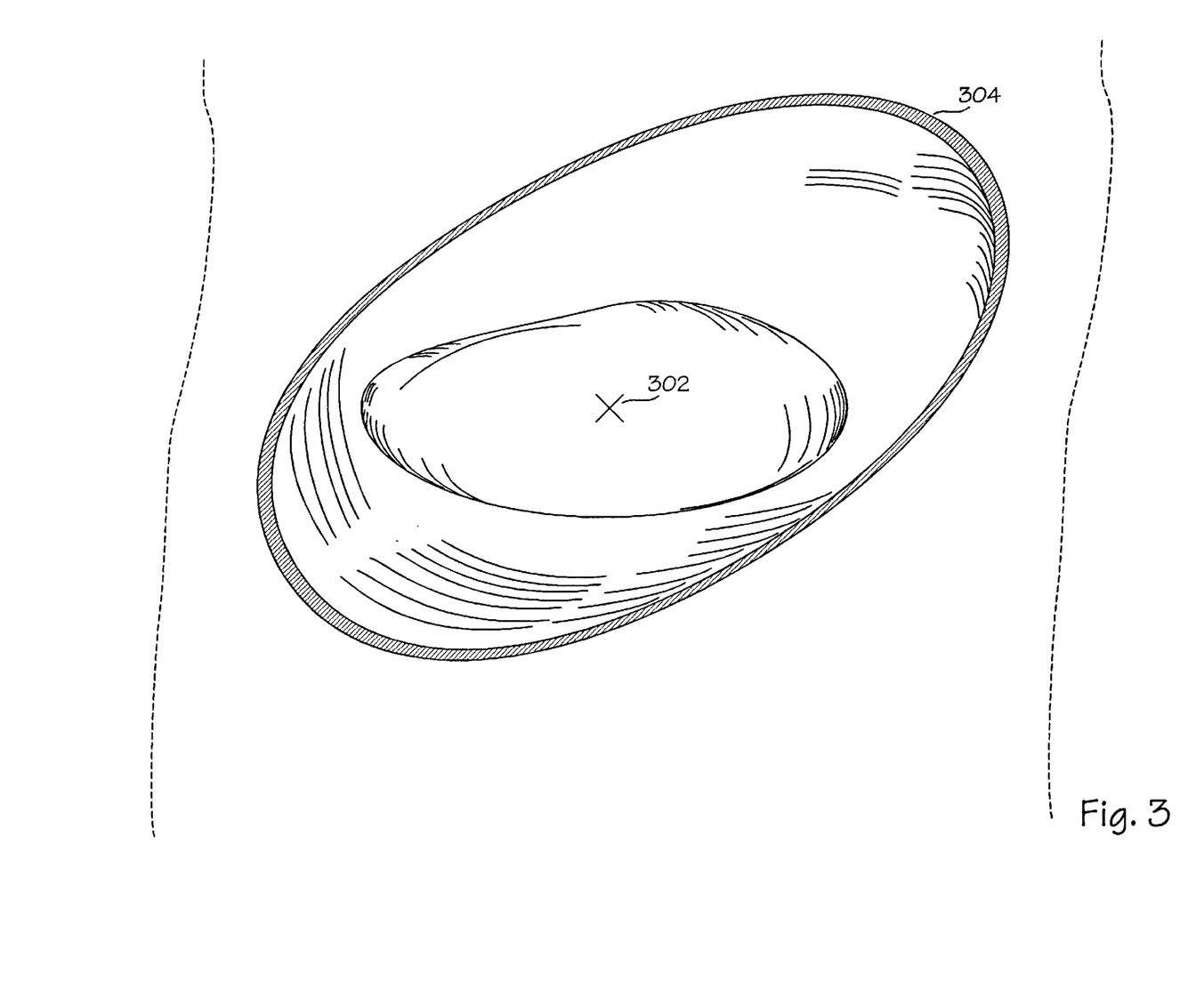
FIG. 3 illustrates an ultrasound image of a first region enclosed in a second region internal to a living organism, wherein the first and second regions consist of different cellular matter.

FIG. 2 is a flow diagram showing the steps for measuring the circumference of the first region according to one embodiment of the present invention. In step 200, further illustrated in FIG. 3, a point 302 known to be within the first region 304 is selected. The selection of the point known to be within the first region may be accomplished automatically or manually. According to one embodiment, a cursor is placed on a video display 130 of ultrasonic system 100 by an operator via an input device such as keyboard 125 or cursor control device 126. Alternatively, a point within the first region to be measured may be selected automatically by ultrasonic system 100.

Figure 4A:
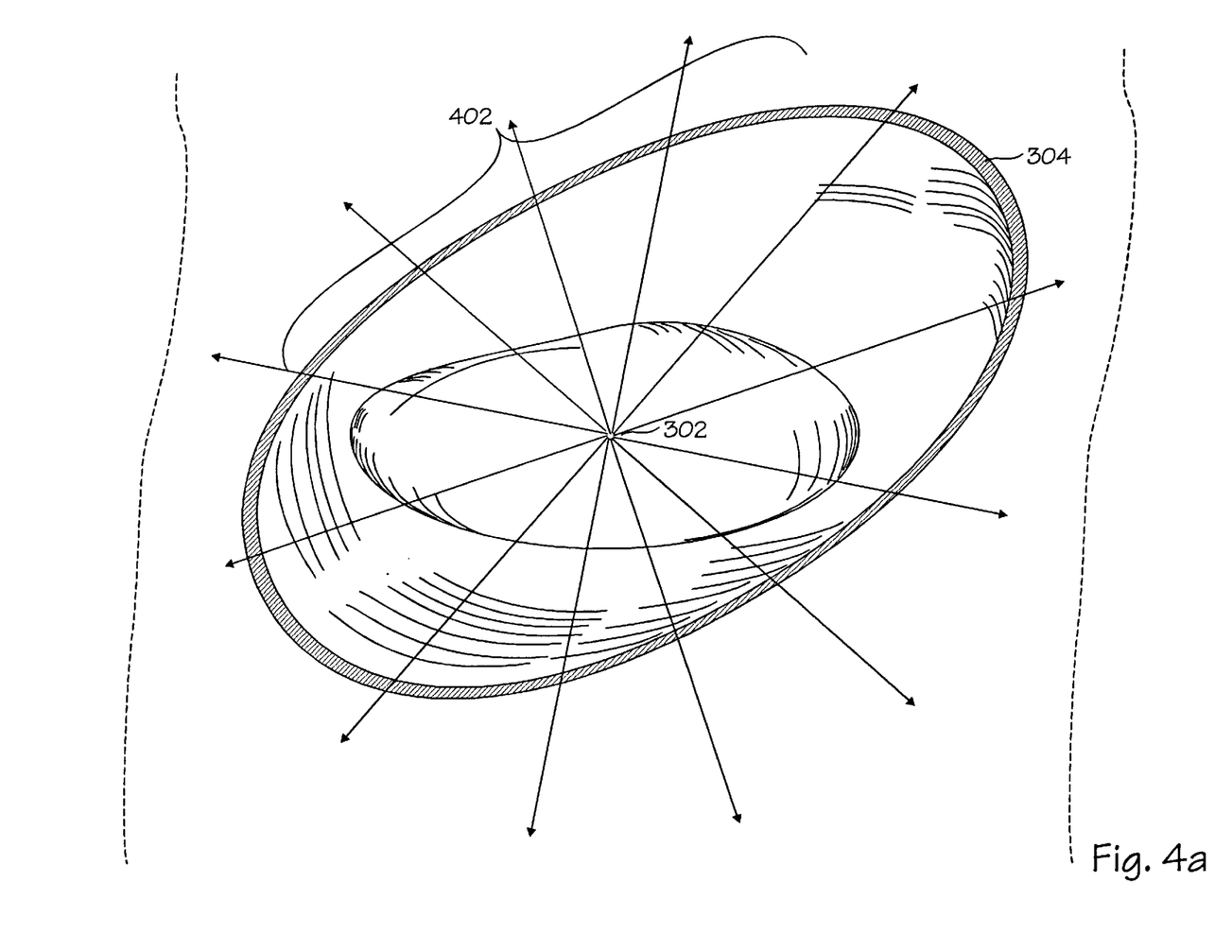
FIG. 4a illustrates a set of radial vectors emanating from a point selected in the first region according to one embodiment of the present invention.

Once a point inside the vessel is selected, in step 210, further illustrated in FIG. 4a, a set of radial vectors 402 are generated, which emanate from the selected point 302. In one embodiment, as illustrated n FIG. 4a, the set of radial vectors are generated so as to emanate in a full circle from the selected point. In alternative embodiments, the set of radial vectors may be generated so as to emanate in a half circle from the selected point.

Figure 4B:
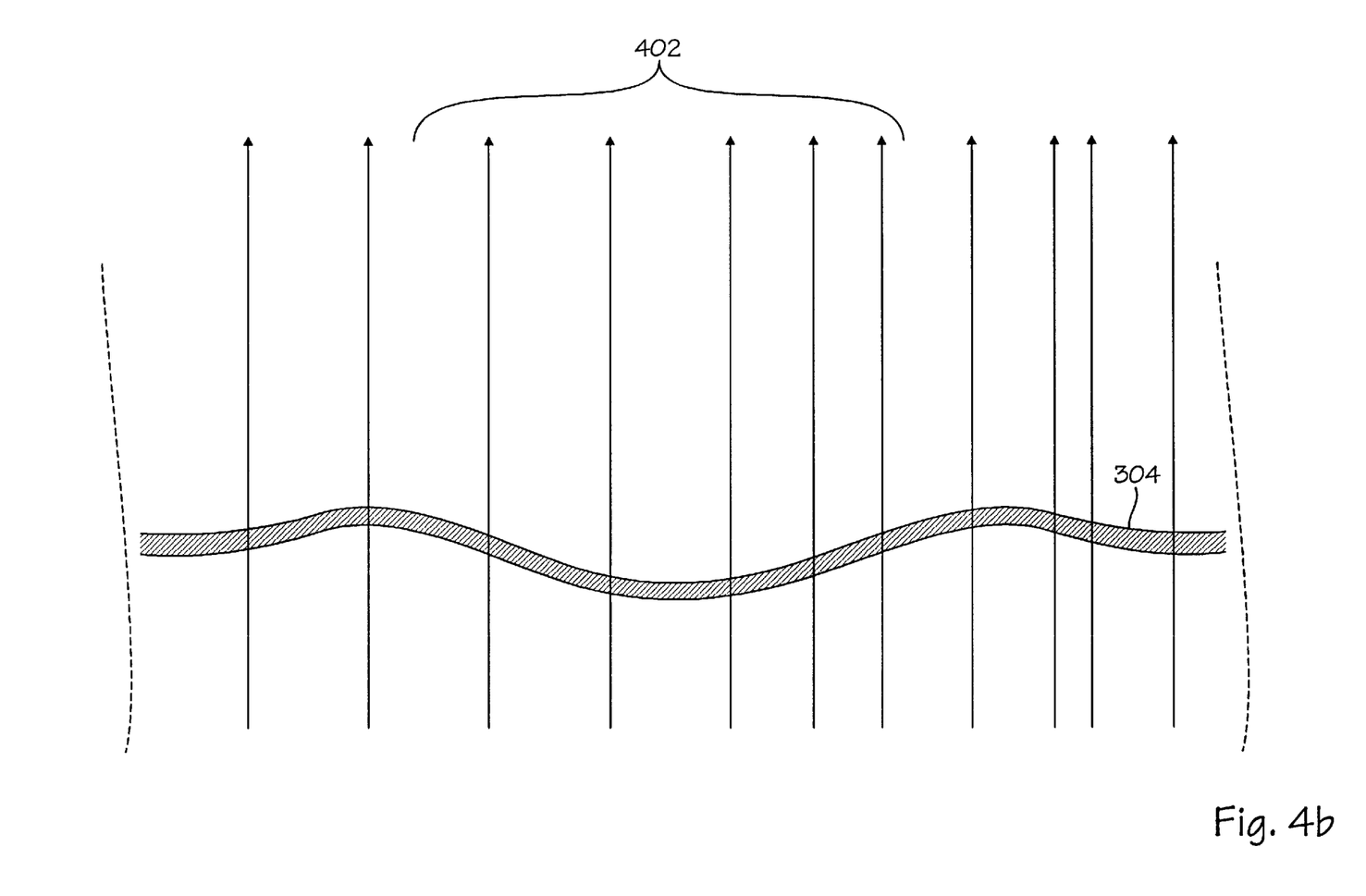
FIG. 4b illustrates a linear horizontal representation of the set of radial vectors according to one embodiment of the present invention.

By generating the set of radial vectors emanating from the selected point, a unique method is provided in one embodiment of the present invention for mapping a closed circular structure into a linear horizontal feature, as shown in FIG. 4b. This unique method of mapping allows each radial vector to cross the surface nearly perpendicular so a one-dimensional filter can be used to enhance images presented in an ultrasound image, including the edges of separate regions.

Another benefit of mapping the enclosed circular region via a set of radial vectors emanating from an interior point is that a significantly less amount of data is necessary to measure the circumference of the selected region in subsequent steps. For example, assuming the image of the first region consist of 480*480 pixels to be displayed by the ultrasonic system 100, the same image can be displayed by the present invention using 16–32 radial vectors. As a result, when using radial vectors the same image, for example, could be displayed using only 240*32 pixels.

Figure 5:
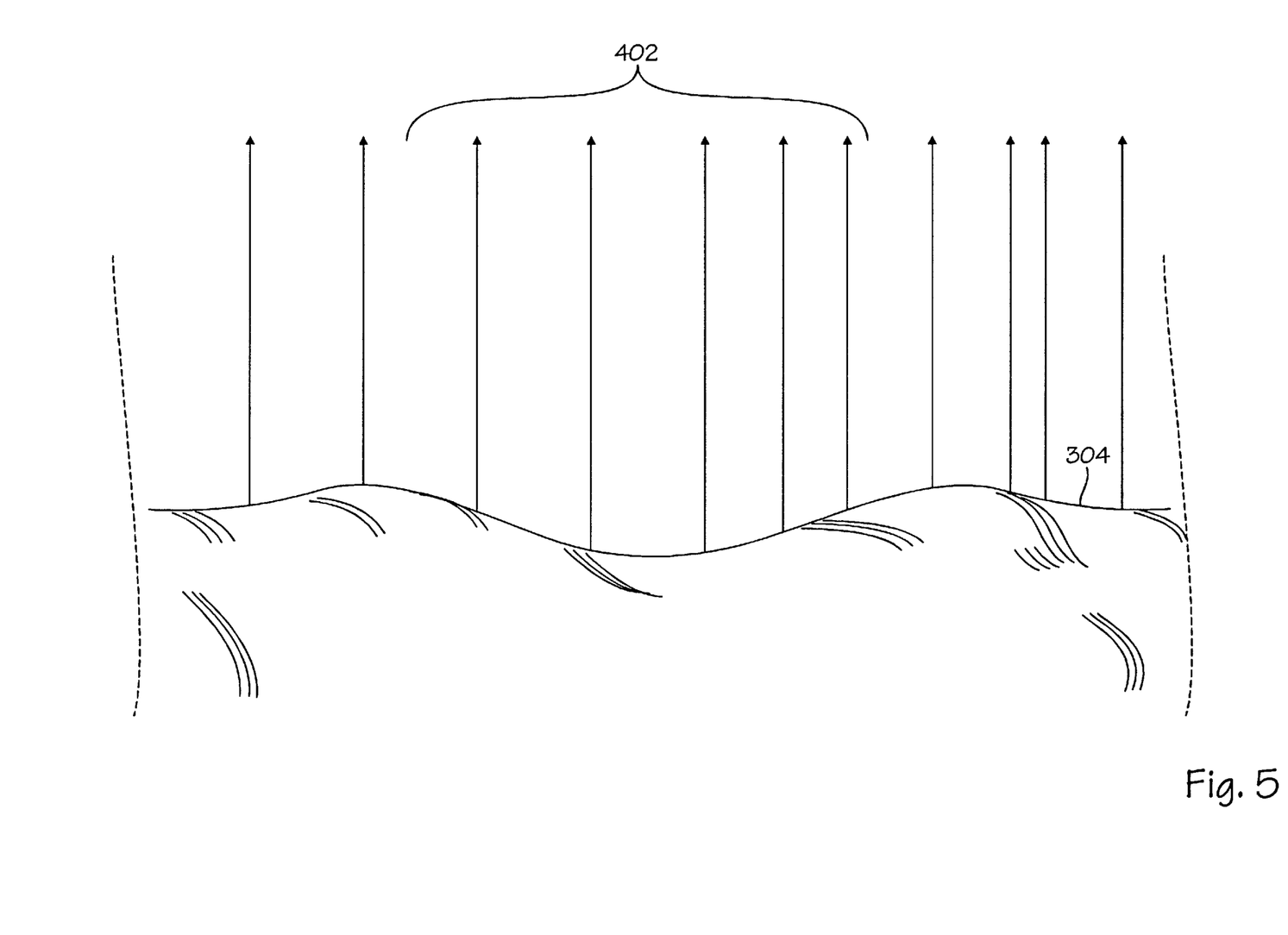
FIG. 5 illustrates application of an edge enhancing filtered ultrasound image according to one embodiment of the present invention.

In step 220, further illustrated in FIG. 5, an edge enhancing filter is applied to images shown in the ultrasonic image of the first and second region to enhance the edges of these images. In one embodiment, a different filter can be used depending on the selected first region. For example, when measuring the head circumference of a fetus, the skull generally shows up as a bright ring on the ultrasound image, and typically the outer edge of the ring is used when making measurements. As a result, it has been empirically determined through testing that the width of the ring is typically about 7 pixels wide when displayed in an ultrasound image. Therefore, in one embodiment, a short edge enhancing filter with weights $\{-1, -1, -1, -1, -1, -1, -1, 0, 1, 1, 1, 1, 1, 11\}$ is used to enhance the edge of a skull in an ultrasound image.

When measuring the abdomen of a fetus, the interior is typically brighter than the exterior with a thin defining edge sometimes present. As a result, in one embodiment, a longer and tapered edge enhancing filter $\{-1, -2, -3, -4, -5, -6, -7, -8, -9, -10, -11, -12, -13, -14, 28, 14, 13, 12, 11, 10, 9, 8, 7, 6, 5, 4, 3, 2, 1\}$ is used to enhance the edge of an abdomen in an ultrasound image.

In step 240, an optimal path that intersects the set of radial vectors is selected based on a predetermined smoothness criteria. More specifically, once the set of radial vectors have been generated, the problem of finding the closed curve of the first region is reduced to finding a path that runs horizontally through the set of radial vectors. In one embodiment, the largest ultrasonic measurement along each radial vector is assumed to be the edge of the first region.

Considering in practice, however, there are often high amplitude features exterior to and interior to the edge of a first region, in alternative embodiments, the present invention imposes the additional constraint that the optimal path be "smooth" in this mapping. That is, the jump in the selected path from one vector to the next be small. In particular, in one embodiment, the following unique equation is used to determine if a particular path is smooth enough to represent the optimal path which represents the edge of the first region.

$$\text{optimal path} = \max \Sigma_{i=\text{vector}} \text{data (radius}(i)) - \alpha(\text{radius}(i) - \text{radius}(i-1))^2$$

The factor alpha in the equation above controls how smooth the curve of a path must be to be selected. If the alpha is set to zero the curve will jump around to the highest value in each vector. If the alpha is set to a relatively larger factor, then the result will be the path with the largest sum. In practice, the optimal smoothness of a curve is obtained for a wide range of alpha values, so the alpha is set empirically. For example, a larger alpha value is used when measuring the abdomen of a fetus then when measuring the head of a fetus because typically the abdomens tend to be rounder than heads and the abdomens tend to be noisier and benefit from additional smoothing. In alternative embodiment, other procedures and equations can be used to select an optimal path having a similar smoothness criteria without departing from the scope of the present invention.

Figure 6:
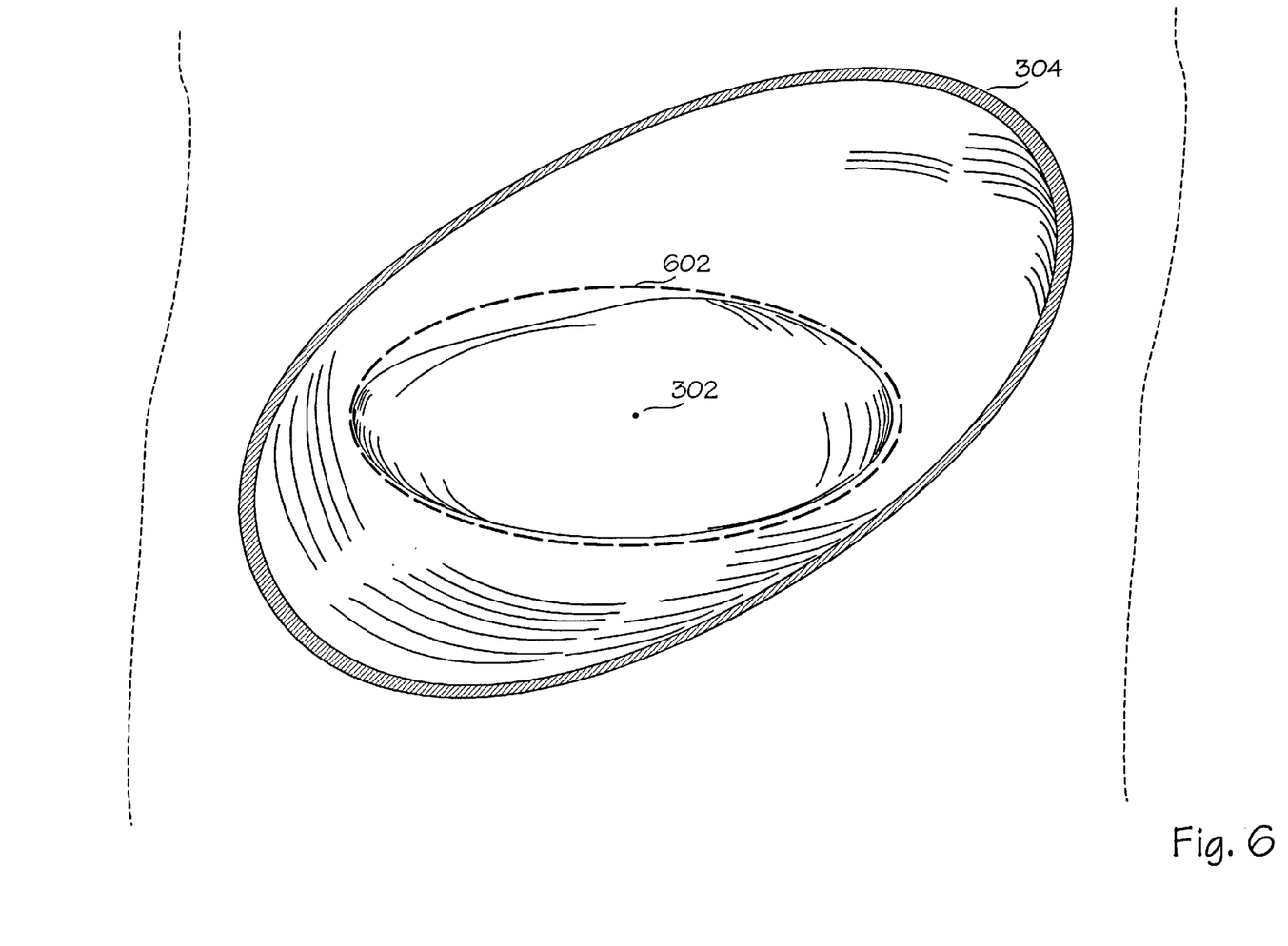
FIG. 6 illustrates a least-square ellipse fitted on the edge of the first region according to one embodiment of the present invention.

In step 250, further illustrated in FIG. 6, the selected path is fitted as an ellipse 602 on the edge 304 of the first region using a method of weighted least squares. In one embodiment, the selected path is reduced to a set of radius and angle values (r(θ)). For example, the ellipse can be written in the form $$r(\theta) = r + a\sin\theta + b\cos\theta$$

The three parameters r, a, and b, along with the x axis and y axis position of the center describe an arbitrary ellipse.

In one embodiment, the following least squares procedure minimizes an "error" function $$\text{error} = \sum_\theta w(\theta)(R(\theta) - r_{trial}(\theta))^2$$

where the trails are over various values of r, a, b, x axis, and y axis positions. As shown in the equation above, the weights (w) used are the "data" values at the selected radii. An iterative procedure is applied. Using the initial cursor position as initial estimate for the x position and y position the values for r, a, and b can be calculated using standard linear inversion techniques. At this stage new values for x and y can be taken by converting the radial values to x and y and taking a linear average. The angles are then recalculated from the new center point and the procedure is repeated until the error value stabilizes.

Afterwards, the ellipse is then drawn on the screen over the original image of the first region, and the circumference can be calculated. In alternative embodiments, alternative equations and procedures can be used to generate an ellipse and minimize the error without departing from the scope of the invention.

Figure 7:
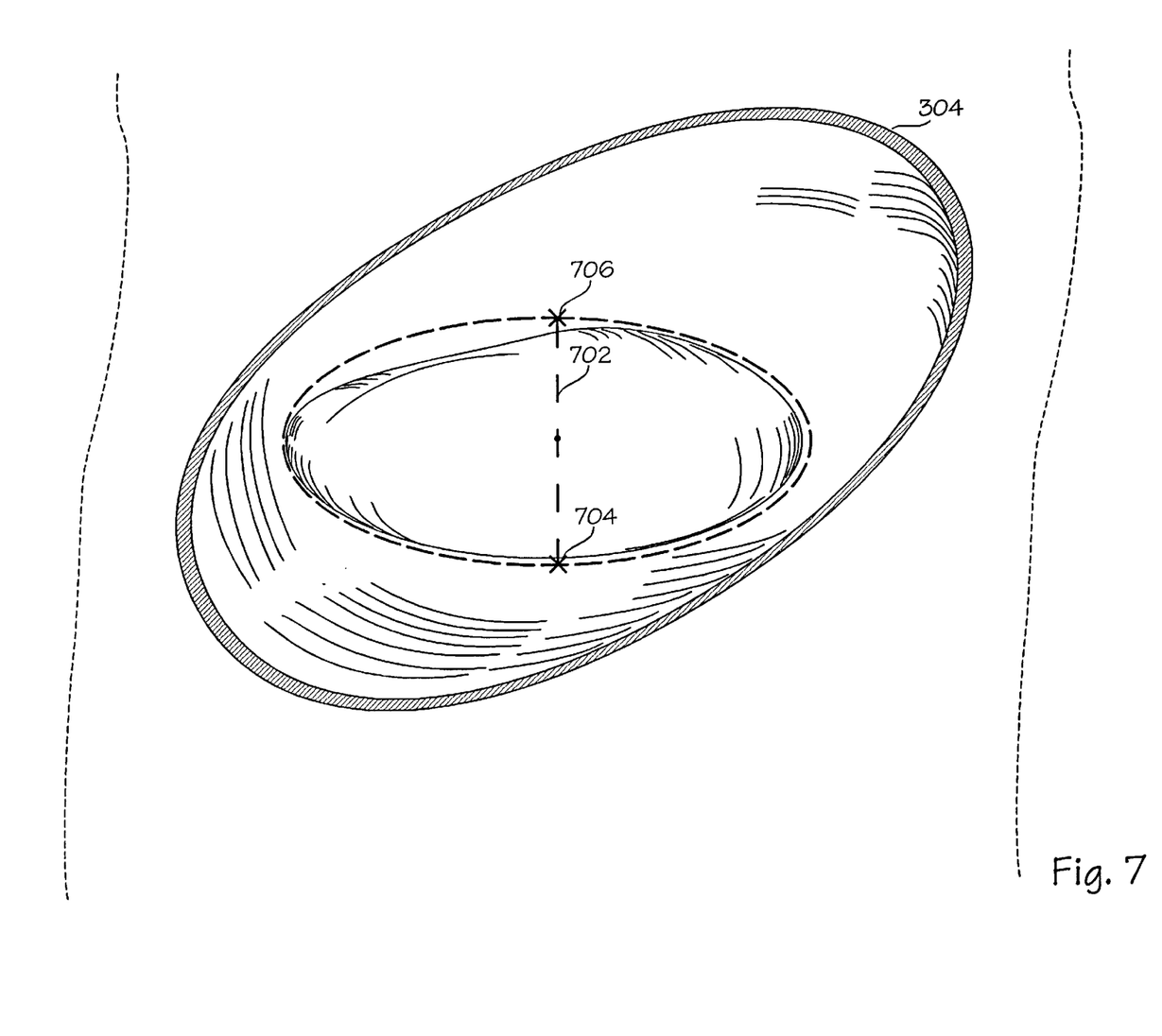
FIG. 7 illustrates a bipolar measurement of the first region according to one embodiment of the present invention.

In step 260, further illustrated in FIG. 7, the BPD measurement of the first region is generated using the short axis 702 of the fitted ellipse, with 20 one end 704 moved to the inside edge of the first region. Once the ellipse is found, the short axis 702 is used as the axis for the BPD measurement. The BPD is traditionally measured from outer edge 706 to inner edge 704. The new radial vectors are taken along the direction of the short axis. The edge enhancing filter is applied to this vectors and the local maximum closest to the original radius estimate is used for one end in the measurement. The same filter is time reversed and applied to the opposing radial vector. The first relative maximum located closer to the center from than original radius is used for the inner edge location. The two cursors 704, 706 are placed on the screen and the distance between them 702 is used as the BPD measurement.

The present invention can be implemented as a computer program product that could be stored on a storage medium having stored thereon instructions which can be used to program a computer to measure the circumference of anatomical internal regions according to the present invention. For example, the present invention can be stored in a memory device, as shown in the memory device coupled to the computer system 100. In addition, the storage medium could include other computer-readable mediums including, but is not limited to, floppy disks, optical disks, CD-ROMs, and magneto-optical disks, ROMs, RAMs, EPROMs, EEPROMs, magnet or optical cards, or any type of media suitable for storing electronic instructions. The instructions stored on such a computer-readable medium could be accessed via a computer-readable medium drive, such as the computer-readable medium drive 132 shown coupled to the computer system 100.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method for measuring a circumference of a first region enclosed in a second region internal to a living organism, wherein the first and second regions consist of different cellular matter, said method comprising the steps of:

a) generating a point inside an interior of said first region;

b) generating a set of radial vectors emanating from said point in the interior of said first region; and c) selecting a path that intersects said set of radial vectors, said path is selected by selecting a distinguishable ultrasonic measurement along the respective radial vectors, using an equation consisting of:

$$\text{optimal path} = \max \Sigma \text{ data (radius(i))} - (\text{radius(i)} - \text{radius(i}-1))^2$$
   $$i = \text{vector; and}$$

d) measuring a length of said path to generate the circumference of said first region.

2. The method of claim 1, wherein the first region is selected from one of a group consisting of a fetus head and a fetus abdominal.

3. The method of claim 1, wherein said path represents an edge of the first region.

4. The method of claim 3, wherein the step of selecting a path further includes selecting a distinguishable ultrasonic measurement along the respective radial vectors that is within a predetermined vertical distance of an ultrasonic measurement selected along an adjacent radial vector.

5. The method of claim 1, further includes the step of fitting said path into an ellipse, wherein the step of fitting said path into said ellipse includes using a weighted least-squares procedure.

6. The method of claim 5, further includes the step of measuring a bipolar diameter of said ellipse, wherein a short axis of said ellipse is used, wherein a first end of the bipolar diameter is measured from an inside of the ellipse and a second opposing end of the bipolar diameter is measured from an outside of the ellipse.

7. A computer-readable medium having stored thereon a plurality of instruction including a first set of instruction for measuring a circumference of a first region enclosed in a second region internal to a living organism, wherein the first and second regions consist of different cellular matter, wherein when said first set of instruction are executed by a processor, said processor performs the steps comprising of:

a) generating a point inside an interior of said first region;

b) generating a set of radial vectors emanating from said point in the interior of said first region; and c) selecting a path that intersects said set of radial vectors, said path is selected by selecting a distinguishable ultrasonic measurement along the respective radial vectors using an equation consisting of:

$$\text{optimal path} = \max \Sigma \text{ data (radius(i))} - (\text{radius(i)} - \text{radius(i}-1)^2 \quad i = \text{vector; and}$$

d) measuring a length of said path to generate the circumference of said first region.

8. The computer-readable medium of claim 7, wherein the first region is selected from one of a group consisting of a fetus head and a fetus abdominal.

9. The computer-readable medium of claim 7, wherein said path represents an edge of the first region.

10. The computer-readable medium of claim 9, wherein the step of selecting a path further includes selecting a distinguishable ultrasonic measurement along the respective radial vectors that is within a predetermined vertical distance of an ultrasonic measurement selected along an adjacent radial vector.

11. The computer-readable medium of claim 7, wherein the first set of instructions further includes additional instructions, which when executed by a processor, cause said processor to further perform the step of fitting said path into an ellipse, wherein the step of fitting said path into said ellipse includes using a weighted least-squares procedure.

12. The computer-readable medium of claim 11, wherein the first set of instructions further includes additional instructions, which when executed by a processor, cause said processor to further perform the step of measuring a bipolar diameter of said ellipse, wherein a short axis of said ellipse is used, wherein a first end of the bipolar diameter is measured from an inside of the ellipse and a second opposing end of the bipolar diameter is measured from an outside of the ellipse.

13. A computer system configured to measure a circumference of a first region enclosed in a second region internal to a living organism, wherein the first and second regions consist of different cellular matter, the computer system comprising:

a first device configured to generate a point inside an interior of said first region;

a second device configured to generate a set of radial vectors emanating from said point in the interior of said first region; and a third device configured to select a path that intersects said set of radial vectors, said path is selected by selecting a distinguishable ultrasonic measurement along the respective radial vectors using an equation consisting of:

$$\text{optimal path} = \max_{i=\text{vector}} \Sigma \text{ data } (\text{radius}(i)) - (\text{radius}(i) - \text{radius}(i-1))^2$$

and a fourth device configured to measure a length of said path to generate the circumference of said first region.

14. The computer system of claim 13, wherein the first region consist of either a fetus head or a fetus abdominal.

15. The computer system of claim 13, wherein said path represents an edge of the first region.

16. The computer system of claim 15, wherein said third device is further configured to select a distinguishable ultrasonic measurement along the respective radial vectors that is within a predetermined vertical distance of an ultrasonic measurement selected along an adjacent radial vector.

17. The computer system of claim 13, further includes a fourth device configured to fit said path into an ellipse using a weighted least-squares procedure.

18. The computer system of claim 17, further includes a fifth device configured to measure a bipolar diameter of said ellipse, wherein a short axis of said ellipse is used, wherein a first end of the bipolar diameter is measured from an inside of the ellipse and a second opposing end of the bipolar diameter is measured from an outside of the ellipse.

* * * * *